United States Patent [19]
Pawloski

[11] 4,418,198
[45] Nov. 29, 1983

[54] SUBSTITUTED PYRIDINE CARBONYL AMINO ETHYL ESTERS OF 2-METHYL-2-PROPENOIC ACID

[75] Inventor: Chester E. Pawloski, Bay City, Mich.

[73] Assignee: The Dow Chemical Company, Midland, Mich.

[21] Appl. No.: 321,356

[22] Filed: Nov. 16, 1981

[51] Int. Cl.³ .................. C07D 213/64; C07D 213/68
[52] U.S. Cl. ..................................... 546/292; 546/286; 546/287; 546/288; 546/289; 546/306; 71/94
[58] Field of Search ............... 546/287, 288, 289, 292, 546/306, 286

[56] References Cited
U.S. PATENT DOCUMENTS

| | | | |
|---|---|---|---|
| 3,249,619 | 5/1966 | Johnston | 546/292 |
| 3,409,624 | 11/1968 | De Selms | 546/292 |
| 3,630,714 | 12/1971 | De Selms | 546/292 |
| 3,701,779 | 10/1972 | Dinninger et ak, | 546/292 |
| 4,180,395 | 12/1979 | Johnston et al. | 546/292 |
| 4,278,809 | 7/1981 | Burdett | 560/206 |

OTHER PUBLICATIONS

Bahr et al., Die Makromolekulare Chemie, vol. 161, (1972), pp. 1–4, 14,15,16,19,37 and 38.

Primary Examiner—Henry R. Jiles
Assistant Examiner—Bernard Dentz
Attorney, Agent, or Firm—Edward P. Gray; Ronald G. Brookens

[57] ABSTRACT

The invention is directed to the novel 2-(((substituted pyridinyl)carbonyl)amino)ethyl esters of 2-methyl-2-propenoic acid and their method of preparation. The compounds are prepared by reacting an appropriately substituted pyridinol, pyridinethiol, aminopyridine, or hydroxyalkyloxypyridine with isocyanatoethyl methacrylate in an appropriate solvent in the presence of an activating agent. These compounds may be utilized as herbicides, fungicides, or both.

17 Claims, No Drawings

SUBSTITUTED PYRIDINE CARBONYL AMINO ETHYL ESTERS OF 2-METHYL-2-PROPENOIC ACID

BACKGROUND OF THE INVENTION

The present invention discloses novel organic compounds and their method of preparation. These compounds are biologically active and may be utilized as herbicides, fungicides or both.

SUMMARY OF THE INVENTION

The present invention is directed to a group of novel, biologically active compounds and their method of preparation. These compounds are represented by the formula:

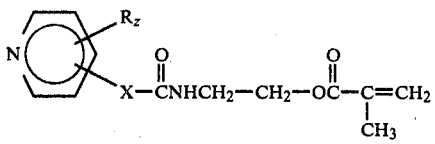

wherein X is oxygen, sulfur, imino(—NH—) or oxyalkyloxy; each R independently represents halo, alkyl, alkyloxy, alkylthio, nitro or cyano, and z is an integer of from zero to four, both inclusive.

As used herein, the term "alkyl" refers to aliphatic, straight or branched chain radicals of from about one to about four carbon atoms inclusive; the term "halo" refers to atoms selected from the group consisting of chlorine, bromine, fluorine and the like.

Of the compounds of the present invention, those preferred for herbicidal or fungicidal use are compounds wherein X is oxygen, R is halo, and z represents the integer 3 or 4. Of the preferred compounds, those compounds wherein R is chloro are particularly preferred.

The compounds of the present invention are biologically active and effective as fungicides, herbicides or both. Typically, the compounds are effective against the causative organisms of fungal diseases such as downey mildew, apple powdery mildew, barley powdery mildew, rice blast, and the like. As herbicides, these compounds are typically effective against a variety of grasses and plants such as pigweed, crabgrass, barnyard grass, yellow foxtail, and sugar beets.

The compounds of the invention may be prepared by the reaction of a suitably substituted pyridinol, pyridinethiol, aminopyridine, or hydroxyalkyloxypyridine with isocyanatoethyl methacrylate represented by the formula:

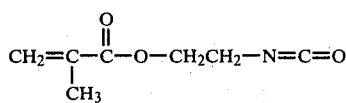

The preparation of the required pyridinols, pyridinethiols, aminopyridines and hydroxyalkyloxypyridines as starting materials for this invention are well known in the art and may be readily prepared by utilizing known procedures. Similarly, the preparation of isocyanatoethyl methacrylate may be carried out by known processes such as the reaction of isopropenyl oxazoline with phosgene in a two phase system of methylene chloride and aqueous caustic.

In the preparation of the compounds of this invention, the reactants are contacted with one another in an inert solvent such as acetone or methylene chloride in the presence of a small amount of activating agent which may be, for example, triethylamine or dibutyltin dilaurate. While the exact proportion of the reactants employed is not critical, the reaction consumes the reactants in amounts representing essentially equimolar proportions and the use of such amounts is preferred. The mixture may then be conveniently stirred at room temperature for a period of time sufficient to assure substantial completion of the reaction and to obtain the desired product. Following reaction, the solvent is removed by conventional techniques and the residue containing the product is recrystallized from a suitable solvent such as n-hexane.

DESCRIPTION OF SOME PREFERRED EMBODIMENTS

The following examples are included to further demonstrate the invention, and are not intended as a limitation thereon.

EXAMPLE 1

2-((((2,3,5,6-Tetrachloro-4-pyridinyl)thio)carbonyl)amino)ethyl ester of 2-methyl-2-propenoic acid 17.5 Grams of 2,3,5,6-tetrachloro-4-pyridinethiol, 9.7 grams of isocyanatoethyl methacrylate, and a few drops of dibutyltin dilaurate (as activating agent) were added to 300 ml of acetone and stirred for 48 hours at room temperature. The solvent was removed under reduced pressure at 30° C. leaving a residual solid, which was then mixed in 400 ml of n-hexane. The n-hexane mixture was filtered and the solid residue obtained was dried, leaving about 22 grams of the desired 2-((((2,3,5,6-tetrachloro-4-pyridinyl)thio)carbonyl)amino)ethyl ester of 2-methyl-2-propenoic acid as a white solid which had a melting point (m.p.) of 104°–105° C.

Following substantially the same procedure as described above, other compounds of the invention were prepared by reacting the appropriately substituted pyridine with isocyanatoethyl methacrylate. Examples 2 through 8 are illustrative.

EXAMPLE 2

2-((((2,4,6-Trichloro-3-pyridinyl)oxy)carbonyl)amino)ethyl ester of 2-methyl-2-propenoic acid, m.p. 86°–89° C.

EXAMPLE 3

2-((((5-Chloro-2-pyridinyl)oxy)carbonyl)amino)ethyl ester of 2-methyl-2-propenoic acid, m.p. 103°–105° C.

EXAMPLE 4

2-(((((2,3,5,6-Tetrachloro-4-pyridinyl)oxy)ethoxy)carbonyl)amino)ethyl ester of 2-methyl-2-propenoic acid, m.p. 67°–69° C.

EXAMPLE 5

2-((((3,5-Dichloro-2,6-difluoro-4-pyridinyl)oxy)carbonyl)amino)ethyl ester of 2-methyl-2-propenoic acid, m.p. 89°–91° C.

EXAMPLE 6

2-((((3,5-Dichloro-2,6-dimethyl-4-pyridinyl)oxy)carbonyl)amino)ethyl ester of 1-methyl-2-propenoic acid, m.p. 112° C. (polymerizing).

EXAMPLE 7

2-((((2,6-Dimethyl-4-pyridinyl)oxy)carbonyl)amino)ethyl ester of 2-methyl-2-propenoic acid, polymerizing upon heating.

EXAMPLE 8

2-(((((6-(Ethylthio)-2-pyridinyl)oxy)carbonyl)amino)ethyl ester of 2-methyl-2-propenoic acid, m.p. 42°-44° C.

EXAMPLE 9

2-((((3,5-Dichloro-2-pyridinyl)oxy)carbonyl)amino)ethyl ester of 2-methyl-2-propenoic acid 3,5-Dichloro-2-pyridinol (15.4 grams) was warmed in 400 ml of acetone until solubilized, and then 15.6 grams of isocyanatoethyl methacrylate and a few drops of dibutyltin dilaurate were added. The mixture was stirred at room temperature for 48 hours, filtered, and the solvent removed under reduced pressure at 30° C. leaving an oily residue. This residue was mixed with 400 ml of n-hexane, filtered, and the filter cake washed with n-hexane and dried. About 24 grams of the 2-((((3,5-dichloro-2-pyridinyl)oxy)carbonyl)amino)ethyl ester of 2-methyl-2-propenoic acid was recovered as a white solid, having a melting point of 74°-77° C. (polymerizing). Distillation of the n-hexane phase yielded about 5 grams of additional product, which was confirmed by NMR spectroscopy.

EXAMPLE 10

2-((((3,4,5,6-Tetrachloro-2-pyridinyl)oxy)carbonyl)amino)ethyl ester of 2-methyl-2-propenoic acid 11.7 Grams of 3,4,5,6-tetrachloro-2-pyridinol, 7.8 grams of isocyanatoethyl methacrylate and a few drops of dibutyltin dilaurate were stirred at room temperature for 48 hours in 200 ml of methylene chloride. The solvent was removed under reduced pressure leaving a solid residue which was mixed with 400 ml of methylene chloride and washed with 200 ml of dilute HCl and 200 ml of water. The product layer was separated, dried over sodium sulfate, filtered and distilled leaving a solid residue. The residue was mixed with 200 ml of n-hexane, filtered and dried leaving about 14.5 grams of the desired product, the 2-((((3,4,5,6-tetrachloro-2-pyridinyl)oxy)carbonyl)amino)ethyl ester of 2-methyl-2-propenoic acid, as a white solid with a melting point of 85° C. (polymerizing). The n-hexane phase was distilled and yielded approximately 2.5 grams of additional product which was confirmed by NMR and IR spectroscopy.

EXAMPLE 11

2-((((2,3,5,6-Tetrachloro-4-pyridinyl)oxy)carbonyl)amino)ethyl ester of 2-methyl-2-propenoic acid 14 Grams of 2,3,5,6-tetrachloro-4-pyridinol, 9.3 grams of isocyanatoethyl methacrylate, and 1 ml of triethylamine were mixed in 200 ml of acetone and stirred at room temperature for about 48 hours. The solvent was removed by evaporation in vacuo leaving a solid residue which was mixed with about 500 ml of n-hexane at about 60° C. and filtered hot. The n-hexane phase was cooled and filtered leaving about 2 grams of solid, determined to be the desired product. The remaining n-hexane filtrate was distilled under reduced pressure and a solid residue obtained. The solid was mixed in about 300 ml of methylene chloride and washed with about 100 ml each of dilute HCl and water. The product layer was separated and dried over sodium sulfate, filtered and distilled to give about 10.5 grams of the desired 2-((((2,3,5,6-tetrachloro-4-pyridinyl)oxy)carbonyl)amino)ethyl ester of 2-methyl-2-propenoic acid, as a white solid with a melting point of 92°-94° C. (polymerizing).

EXAMPLE 12

2-((((3,5,6-Trichloro-2-pyridinyl)oxy)carbonyl)amino)ethyl ester of 2-methyl-2-propenoic acid 19.7 Grams of 3,5,6-trichloro-2-pyridinol was reacted with 15.5 grams of isocyanatoethyl methacrylate in 200 ml of acetone and 1 ml of triethylamine as an activating agent. The reactants were stirred at reflux temperature for about 12 hours, cooled and filtered. The solid residue from the filtration was slurried in hot n-hexane and filtered again. The n-hexane phase was distilled under reduced pressure and yielded about 2.5 grams of white solid determined to be the desired, 2-((((3,5,6-trichloro-2-pyridinyl)oxy)carbonyl)amino)ethyl ester of 2-methyl-2-propenoic acid, which melted at 84°-91° C.

EXAMPLE 13

2-((((2,3,5-Trichloro-4-pyridinyl)oxy)carbonyl)amino)ethyl ester of 2-methyl-2-propenoic acid 10 Grams of 2,3,5-trichloro-4-pyridinol, 7.8 grams of isocyanatoethyl methacrylate, and 1 ml of triethylamine were mixed in 200 ml of acetone and stirred for 48 hours at room temperature. The solvent was removed under reduced pressure at 30° C., and the resulting solids slurried in 400 ml of n-hexane at 60° C. and filtered hot. The solid residue from this filtration was mixed in 300 ml of methylene chloride and washed with 200 ml each of dilute HCl and water. The product layer was separated, dried over sodium sulfate, filtered and distilled leaving about 10.5 grams of desired product, the 2-((((2,3,5-trichloro-4-pyridinyl)oxy)carbonyl)amino)ethyl ester of 2-methyl-2-propenoic acid, as a white solid melting at 94° C. (polymerizing).

The compounds of the present invention may be used as fungicides, herbicides or both. For these uses, one or more of the compounds may be used in unmodified form, or may be formulated into fungicidal or herbicidal compositions. For instance, compounds of this invention may be employed as a dispersion in a finely divided solid and applied as a dust. The compounds may also be formulated into aqueous compositions with or without the use of a wetting agent and applied as a spray. Similarly, the compounds may be employed in liquid organic compositions, water-in-oil or oil-in-water emulsions or aqueous dispersions with or without the use of emulsifying, wetting or dispersing agents.

Not all compounds or the compositions containing them may be equally effective at similar concentrations or against similar plant or fungal organisms. While the exact amount of compound or composition employed is not critical, good results are obtained when the plant, organism, and/or their habitat is contacted with a herbicidally or fungicidally effective amount of one or more of the compounds or compositions containing them. The term "effective amount" refers to a fungicidal concentration of from about 6.2 to 1,200 parts per million by weight or about 4 pounds per acre depending on the mode of application. Similarly, a herbicidally "effective amount" refers to a concentration of from about 62.5 to about 4,000 parts per million by weight or about 0.25 to about 10 pounds per acre depending upon the mode of application.

In a representative operation, seeds representing grassy weeds, broadleaf weeds and broadleaf crops were planted and the soil treated with varying concentrations of one of the compounds being tested for pre-emergence activity. The data are compiled in Table I and the results expressed in percent kill of the particular plant species.

TABLE I

| PLANT | EXAMPLE NUMBER | | | | | | |
|---|---|---|---|---|---|---|---|
| | 2 | 4 | 5 | 7 | 11 | 12 | 13 |
| Cotton | NT[5] | 0[4] | 100[4] | 100[4] | 40[3] | 60[4] | 60[3] |
| Pigweed | 100[4] | 100[4] | 100[4] | 0[4] | 80[3] | 100[4] | 100[3] |
| Crabgrass | NT[5] | 80[4] | 100[4] | NT[5] | 100[3] | 99[4] | 100[3] |
| Corn | NT[5] | NT[5] | 50[3] | NT[5] | 80[3] | NT[5] | 98[3] |
| Sorghum/Milo | NT[5] | NT[5] | 80[1] | NT[5] | 90[3] | NT[5] | 99[3] |
| Barnyard Grass | NT[5] | 30[4] | 100[4] | NT[5] | 99[3] | NT[5] | 100[3] |
| Sugar Beets | NT[5] | NT[5] | NT[5] | NT[5] | 80[3] | NT[5] | 100[3] |
| Wild Oats | NT[5] | 0[4] | 100[4] | NT[5] | 98[2] | NT[5] | 95[3] |
| Yellow Foxtail | NT[5] | 0[4] | 100[4] | NT[5] | 98[3] | 30[4] | 98[3] |
| Jimson Weed | NT[5] | NT[5] | NT[5] | NT[5] | 60[3] | NT[5] | 60[3] |
| Morning Glory | NT[5] | 80[4] | 100[4] | NT[5] | 95[2] | NT[5] | 60[3] |
| Nutsedge | NT[5] | NT[5] | NT[5] | NT[5] | 60[3] | NT[5] | 100[3] |

[1]Concentration applied - 0.25 pounds per acre
[2]Concentration applied - 2.0 pounds per acre
[3]Concentration applied - 4.0 pounds per acre
[4]Concentration applied - 10.0 pounds per acre
[5]NT — Not Tested In a similar operation, the post-emergence activity of the 2-((((2,3,5-trichloro-4-pyridinyl)oxy)carbonyl)amino)ethyl ester of 2-methyl-2-propenoic acid was tested. Various plant species were grown in six separate plots so that each plot contained all of the species. The plants were grown to a height of about four inches, and then each plot was sprayed to run-off with one of six aqueous compositions of test compound prepared in concentrations of 2000, 1000, 500, 250, 125 and 62.5 parts per million (ppm) by weight. The plants were then placed in an environment conducive to growth and were evaluated two weeks later. The results of the test are summarized in Table II, and are expressed in terms of percent kill of the particular plant species.

TABLE II

| | (EXAMPLE 13) | | | | | |
|---|---|---|---|---|---|---|
| | CONCENTRATION (ppm) | | | | | |
| PLANT | 2000 | 1000 | 500 | 250 | 125 | 62.5 |
| Cotton | 100 | 100 | 100 | 100 | 70 | 70 |
| Soybean | 95 | 95 | 95 | 90 | 90 | 80 |
| Sugar Beets | 100 | 100 | 100 | 100 | 100 | 100 |
| Jimson Weed | 100 | 100 | 100 | 100 | 100 | 98 |
| Pigweed | 100 | 100 | 100 | 100 | 100 | 100 |
| Corn | 100 | 95 | 95 | 95 | 100 | 100 |
| Rice | 99 | 98 | 95 | 95 | 70 | 10 |
| Crabgrass | 100 | 100 | 100 | 100 | 100 | 100 |
| Johnson Grass | 100 | 100 | 100 | 100 | 100 | 98 |

In substantially the same operation as described above, the 2-((((5-chloro-2-pyridinyl)oxy)carbonyl)amino)ethyl ester of 2-methyl-2-propenoic acid, and the 2-((((2,3,5,6-tetrachloro-4-pyridinyl)thio)carbonyl)amino)ethyl ester of 2-methyl-2-propenoic acid was tested for post-emergence activity. When utilized as an aqueous spray at 4000 ppm by weight, the compounds showed 80 percent control of morning glory and 100 percent control of velvet weed respectively.

In other operations, compounds of the present invention demonstrated activity as antifungal agents. The 2-((((3,4,5,6-tetrachloro-2-pyridinyl)oxy)carbonyl)amino)ethyl ester of 2-methyl-2-propenoic acid, and the 2-((((2,3,5,6-tetrachloro-4-pyridinyl)oxy)carbonyl)amino)ethyl ester of 2-methyl-2-propenoic acid showed substantially complete control (93 and 100 percent, respectively) of the causative organism of apple powdery mildew when separately employed at a concentration of 100 ppm by weight. Similarly, the 2-((((3,5-dichloro-2,6-dimethyl-4-pyridinyl)oxy)carbonyl)amino)ethyl ester of 2-methyl-2-propenoic acid showed 90 percent control of the causative organism of rice blast when tested at a concentration of 500 ppm by weight. The 2-((((6-ethylthio-2-pyridinyl)oxy)carbonyl)amino)ethyl ester of 2-methyl-2-propenoic acid and the 2-((((2,3,5,6-tetrafluoro-4-pyridinyl)amino)carbonyl)amino)ethyl ester of 2-methyl-2-propenoic acid each demonstrated activity as anti-fungal agents by completely killing the causative organism of verticillium wilt when tested individually at a concentration of 100 ppm by weight. Also, the 2-((((2,3,5-trichloro-4-pyridinyl)oxy)carbonyl)amino)ethyl ester of 2-methyl-2-propenoic acid showed substantially total kill of the causative organism of barley powdery mildew when employed as an aqueous suspension at a concentration of 75 ppm by weight. The fungicidal activity of the 2-((((3,5-dichloro-2-pyridinyl)oxy)carbonyl)amino)ethyl ester of 2-methyl-2-propenoic acid was similarly exhibited by its substantially complete kill of the causative organism of apple powdery mildew when applied to the root system and foliage of test plants at a concentration of 500 ppm by weight.

What is claimed is:

1. A compound corresponding to the formula:

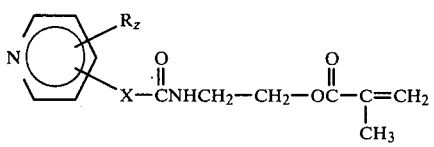

wherein X is oxygen, sulfur, imino (—NH—) or oxyalkyloxy of one to four carbon atoms both inclusive; each R independently represents halo, alkyl of one to four carbon atoms both inclusive, alkyloxy of one to four carbon atoms both inclusive, alkylthio of one to four carbon atoms both inclusive, nitro or cyano; and z is an integer of from zero to four, both inclusive, provided that when X is imino (—NH—) z is not zero and further provided that when X is imino and z is the integer one, R is a substituent other than alkyl of one to four carbon atoms.

2. The compound of claim 1 wherein X is oxygen, R is halo, and z is the integer three.

3. The compound of claim 1 wherein X is oxygen, R is halo, and z is the integer four.

4. The compound of claim 1 which is the 2-((((2,3,5,6-tetrachloro-4-pyridinyl)thio)carbonyl)amino(ethyl ester of 2-methyl-2-propenoic acid.

5. The compound of claim 1 which is the 2-((((2,4,6-trichloro-3-pyridinyl)oxy)carbonyl)amino)ethyl ester of 2-methyl-2-propenoic acid.

6. The compound of claim 1 which is the 2-((((5-chloro-2-pyridinyl)oxy)carbonyl)amino)ethyl ester of 2-methyl-2-propenoic acid.

7. The compound of claim 1 which is the 2-((((3,5-dichloro-2,6-difluoro-4-pyridinyl)oxy)carbonyl)amino)ethyl ester of 2-methyl-2-propenoic acid.

8. The compound of claim 1 which is the 2-((((3,5-dichloro-2,6-dimethyl-4-pyridinyl)oxy)carbonyl)amino)ethyl ester of 2-methyl-2-propenoic acid.

9. The compound of claim 1 which is the 2-((((2,6-dimethyl-4-pyridinyl)oxy)carbonyl)amino)ethyl ester of 2-methyl-2-propenoic acid.

10. The compound of claim 1 which is the 2-((((6-(ethylthio)-2-pyridinyl)oxy)carbonyl)amino)ethyl ester of 2-methyl-2-propenoic acid.

11. The compound of claim 1 which is the 2-((((3,5-dichloro-2-pyridinyl)oxy)carbonyl)amino)ethyl ester of 2-methyl-2-propenoic acid.

12. The compound of claim 1 which is the 2-(((((2,3,5,6-tetrachloro-4-pyridinyl)oxy)ethoxy)carbonyl)amino)ethyl ester of 2-methyl-2-propenoic acid.

13. The compound of claim 1 which is the 2-((((3,4,5,6-tetrachloro-2-pyridinyl)oxy)carbonyl)amino)ethyl ester of 2-methyl-2-propenoic acid.

14. The compound of claim 1 which is the 2-((((3,4,6-trichloro-2-pyridinyl)oxy)carbonyl)amino)ethyl ester of 2-methyl-2-propenoic acid.

15. The compound of claim 1 which is the 2-(((((2,3,5,6-tetrafluoro-4-pyridinyl)amino)carbonyl)amino)ethyl ester of 2-methyl-2-propenoic acid.

16. The compound of claim 2 which is the 2-((((2,3,5-trichloro-4-pyridinyl)oxy)carbonyl)amino)ethyl ester of 2-methyl-2-propenoic acid.

17. The compound of claim 3 which is the 2-((((2,3,5,6-tetrachloro-4-pyridinyl)oxy)carbonyl)amino)ethyl ester of 2-methyl-2-propenoic acid.

* * * * *

UNITED STATES PATENT AND TRADEMARK OFFICE
CERTIFICATE OF CORRECTION

PATENT NO. : 4,418,198
DATED : November 29, 1983
INVENTOR(S) : Chester E. Pawloski It is certified that error appears in the above—identified patent and that said Letters Patent is hereby corrected as shown below:

Title page, first column, under "U.S. Patent Documents", line 4, "Dinninger et ak," should read --Dinninger et al.--

Title page, second column, under "Abstract", first line, "The" should read --This--.

Column 3, line 4, "1-methyl" should read --2-methyl--.

Column 5, line 64, "was" should read --were--.

Column 6, line 61, "(ethyl" should read --)ethyl--.

Column 8, line 7, "3,4,6-" should read --3,5,6- --.

Signed and Sealed this

Thirty-first Day of July 1984

[SEAL]

Attest:

GERALD J. MOSSINGHOFF

Attesting Officer      Commissioner of Patents and Trademarks